(12) United States Patent
Yashiro et al.

(10) Patent No.: US 7,318,818 B2
(45) Date of Patent: Jan. 15, 2008

(54) INDWELLING CATHETER SET

(75) Inventors: Kenji Yashiro, Tatebayashi (JP); Yoshio Higaki, Tatebayashi (JP); Tsuyoshi Yano, Tatebayashi (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/819,129

(22) Filed: Apr. 7, 2004

(65) Prior Publication Data
US 2004/0204691 A1 Oct. 14, 2004

(30) Foreign Application Priority Data
Apr. 8, 2003 (JP) ............................. 2003-103828

(51) Int. Cl.
*A61M 5/178* (2006.01)
(52) U.S. Cl. .............................. 604/164.07; 604/167.02
(58) Field of Classification Search ................................
604/167.01–167.04, 164.01, 164.04, 164.07, 604/253, 257, 264
See application file for complete search history.

(56) References Cited

U.S. PATENT DOCUMENTS

| 4,512,766 | A | * | 4/1985 | Vailancourt | ............ | 604/167.03 |
|---|---|---|---|---|---|---|
| 4,966,588 | A | * | 10/1990 | Rayman et al. | ......... | 604/165.02 |
| 5,176,662 | A | | 1/1993 | Bartholomew et al. | ..... | 604/283 |
| 6,056,718 | A | | 5/2000 | Funderburk et al. | .......... | 604/93 |
| 6,488,663 | B1 | * | 12/2002 | Steg | ...................... | 604/164.08 |
| 6,572,586 | B1 | * | 6/2003 | Wojcik | .................. | 604/165.01 |
| 6,673,440 | B2 | * | 1/2004 | Douglas et al. | ............. | 428/336 |
| 7,008,404 | B2 | * | 3/2006 | Nakajima | ................... | 604/158 |
| 2002/0055722 | A1 | | 5/2002 | Douglas et al. | ............. | 604/272 |

FOREIGN PATENT DOCUMENTS

| WO | 01/52617 A2 | 7/2001 |
|---|---|---|
| WO | 02/07804 A1 | 1/2002 |
| WO | 02/094352 A2 | 11/2002 |

* cited by examiner

*Primary Examiner*—Kevin C. Sirmons
*Assistant Examiner*—Andrew Gilbert
(74) *Attorney, Agent, or Firm*—Kubovcik & Kubovcik

(57) ABSTRACT

An indwelling catheter set comprises a cannula housing. The cannula housing comprises: (a) a catheter disposed substantially in the axial direction and formed into a hollow body opened at its distal and proximal ends; and (b) a catheter hub comprising a through bore extending substantially in the axial direction for inserting the proximal portion of the catheter therethrough. The catheter is adhered or welded to the catheter hub.

5 Claims, 15 Drawing Sheets

FIG.8(A)
FIG.8(B)
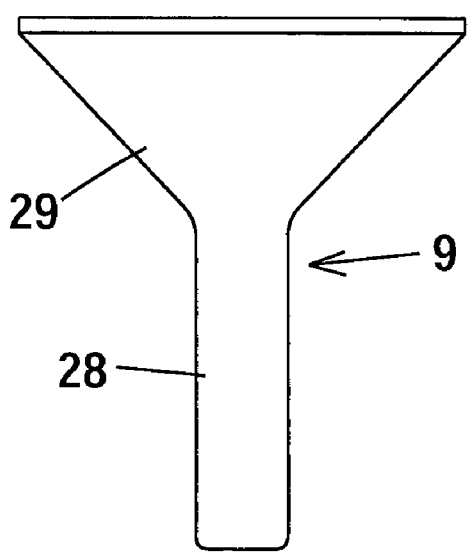
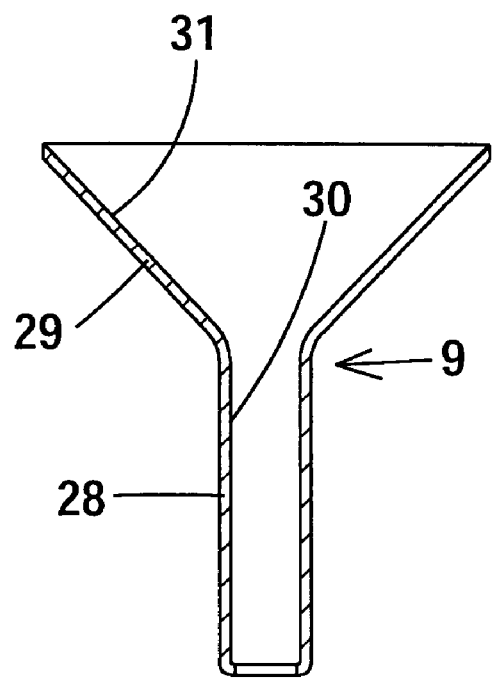

INDWELLING CATHETER SET

This application claims foreign priority to JAPAN 2003-103828 filed on Apr. 8, 2003.

FIELD OF THE INVENTION

The present invention relates to various indwelling catheter sets for performing solution infusion, blood transfusion, blood collection, and dialysis therapy (for example, a hypodermic injection set for a drug solution such as an insulin administration set).

DESCRIPTION OF THE RELATED

There is an administration set for administering insulin discontinuously or continuously having a female luer taper, and a needle and a male luer taper to be detachably connected to the female luer taper, respectively (for example, see U.S. Pat. No. 6,056,718).

In this set, the female luer taper includes (a) a hollow catheter disposed in the axial direction and having openings at axial ends thereof, (b) a catheter hub including an axially extending through bore through which the proximal portion of the catheter is inserted from its distal end, and (c) a fixing pin (caulking pin) formed into a hollow body having openings at its axial ends thereof for fixing the catheter to the catheter hub.

When fixing the catheter to the catheter hub, the fixing pin is press-fitted into the proximal end of the catheter to enlarge the proximal portion of the catheter radially outwardly, and in this state, the catheter and the fixing pin are press-fitted into the through bore of the catheter hub, and then the proximal portion of the catheter is clamped and fixed between the fixing pin and the inner surface of the through bore.

The proximal end portion of the fixing pin is proximally flared so as to be enlarged toward the proximal end. Therefore, when the needle is connected to the female luer taper, and the insertion needle of the needle is inserted into a plug of the female luer taper and the catheter, the catheter is guided on the inner surface of the proximal end of the fixing pin so as to be easily inserted into the insertion needle.

In the above-described U.S. Pat. No. 6,056,718, the catheter is fixed to the catheter hub with the fixing pin as described above, and hence many process steps for fixing the catheter are required and, in addition, the fixing pin is also required, which actually increases the manufacturing cost of the female luer taper, that is, the administration set.

In addition, since the machining accuracy of the fixing pin varies, when a fixing pin larger than the standard is inserted into the catheter hub together with the catheter, there is a risk that the catheter hub is cracked, or the catheter is broken by the tip of the fixing pin. In contrast, when a fixing pin smaller than the standard is used, there is a risk that the catheter cannot be fixed desirably to the catheter hub, and hence leakage of liquid occurs.

BRIEF SUMMARY OF THE INVENTION

As a result of earnest investigations made by the inventors to solve the problems associated with the conventional techniques, the invention has been completed.

It is a first object of the present invention to provide an indwelling catheter set in which the process steps for fixing the catheter can be reduced in comparison with the fixing method using a fixing pin in the related art, and the fixing pin for fixing the catheter, which is required in the related art, can be eliminated, so that the manufacturing cost of the female luer taper, that is, the indwelling catheter set, can be reduced.

It is a second object of the present invention to provide an indwelling catheter set in which the risks of cracking of the catheter hub or breakage of the catheter by the tip of the fixing pin, or occurrence of leakage of liquid caused by variations in machining accuracy of the fixing pin can be eliminated.

The above-mentioned objects and other objects of the present invention will be clarified furthermore in the following description, and these objects are attained by the present invention comprising the constitution mentioned below.

The present invention relates to an indwelling catheter set comprising a cannula housing, (a) a catheter disposed substantially in the axial direction and formed into a hollow body opened at its distal and proximal ends; and (b) a catheter hub comprising a through bore extending substantially in the axial direction for inserting a proximal portion of the catheter therethrough, wherein the catheter is adhered or welded to the catheter hub.

The catheter and the catheter hub may be formed of the same plastic material by injection molding.

The outer surface of the catheter may be roughened by surface processing.

A proximal end portion of the catheter may be flared so as to be enlarged toward its proximal end.

The indwelling catheter set may comprise:

(a) the cannula housing according to claim 1; and (b) an insertion hub and an infusion hub to be detachably connected to the cannula housing, respectively, the insertion hub comprising:

(a) an insertion needle disposed substantially in the axial direction and formed into a hollow body opened at its distal and proximal ends, the insertion needle being detachably inserted into a plug and the catheter from proximal ends thereof when connecting the insertion hub and the cannula housing; and (b) an insertion needle hub provided at a proximal portion of the insertion needle, the insertion needle hub being detachably connected to the catheter hub from its proximal end when connecting the insertion hub and the cannula housing, the infusion hub comprising:

(a) an infusion needle for feeding liquid disposed substantially in the axial direction and formed into a hollow body opened at its distal and proximal ends, the infusion needle being detachably inserted into the plug from its proximal end, when connecting the infusion hub and the cannula housing, so as to communicate with the catheter; and (b) an infusion tubing hub provided at a proximal portion of the infusion needle, the infusion tubing hub being detachably connected to the catheter hub from its proximal end when connecting the infusion hub and the cannula housing.

A proximal portion of the through bore may be formed as a connecting port for feeding liquid, the plug formed of resilient material for sealing the connecting port may be inserted into the connecting port from its proximal end, a guide may be inserted into a portion of the connecting port, which is disposed proximally of the plug, the guide may be formed into a hollow body opened at its distal and proximal ends for preventing the plug from dropping off the connecting port, the guide may allow detachable insertion of the insertion needle and the infusion needle from proximal ends thereof, at least a proximal portion of the interior of the guide may be formed into a tapered bore tapered toward the distal end of the guide, and at least the proximal portion of the interior of the guide may have an inner surface for guiding the insertion needle and the infusion needle to a substantially axial center of the connecting port.

The guide comprises in the interior:

(a) a straight bore forming a distal portion of the interior of the guide, the straight bore having an inner diameter substantially constant in the axial direction; and (b) the tapered bore forming the proximal portion of the interior of the guide.

BRIEF DESCRIPTION OF THE DRAWINGS

FIG. 1 to FIG. 13 show a first embodiment of the present invention, and FIG. 1 is a plan view, partly in cross section.

FIG. 2 is a vertical cross section of FIG. 1.

FIG. 3 is a partly enlarged view of FIG. 2.

FIG. 4 is an exploded view of FIG. 2.

FIG. 5 is a plan view, partly in cross section, of a cannula housing in FIG. 1.

FIG. 6 is a partly enlarged view of FIG. 4.

FIG. 7 is a partly enlarged view of FIG. 4.

FIG. 8A is a side view of a guide in FIG. 7, FIG. 8B is a vertical cross section of FIG. 8A.

FIG. 9 is a plan view, partly in cross section, of an insertion hub in FIG. 1.

FIG. 10 is a plan view, partly in cross section, showing a state in which the insertion hub in FIG. 1 is replaced by an infusion hub.

FIG. 11 is a vertical cross section of FIG. 10.

FIG. 12 is a plan view, partly in cross section, of an infusion hub in FIG. 11.

FIG. 14 is a vertical cross section.

FIG. 15 is a vertical cross section showing the proximal portion of the catheter in FIG. 14.

FIG. 16 and FIG. 17 show a third embodiment of the present invention, and FIG. 16 is a vertical cross section.

DETAILED DESCRIPTION OF THE INVENTION

Referring now to FIG. 1 to FIG. 13, the first embodiment in which the present invention is applied to an insulin administration set will be described. As shown in FIG. 1 to FIG. 4, and FIG. 10 and FIG. 12, the administration set includes a cannula housing 1, an insertion hub 2, and an infusion hub 3.

Figure 5:
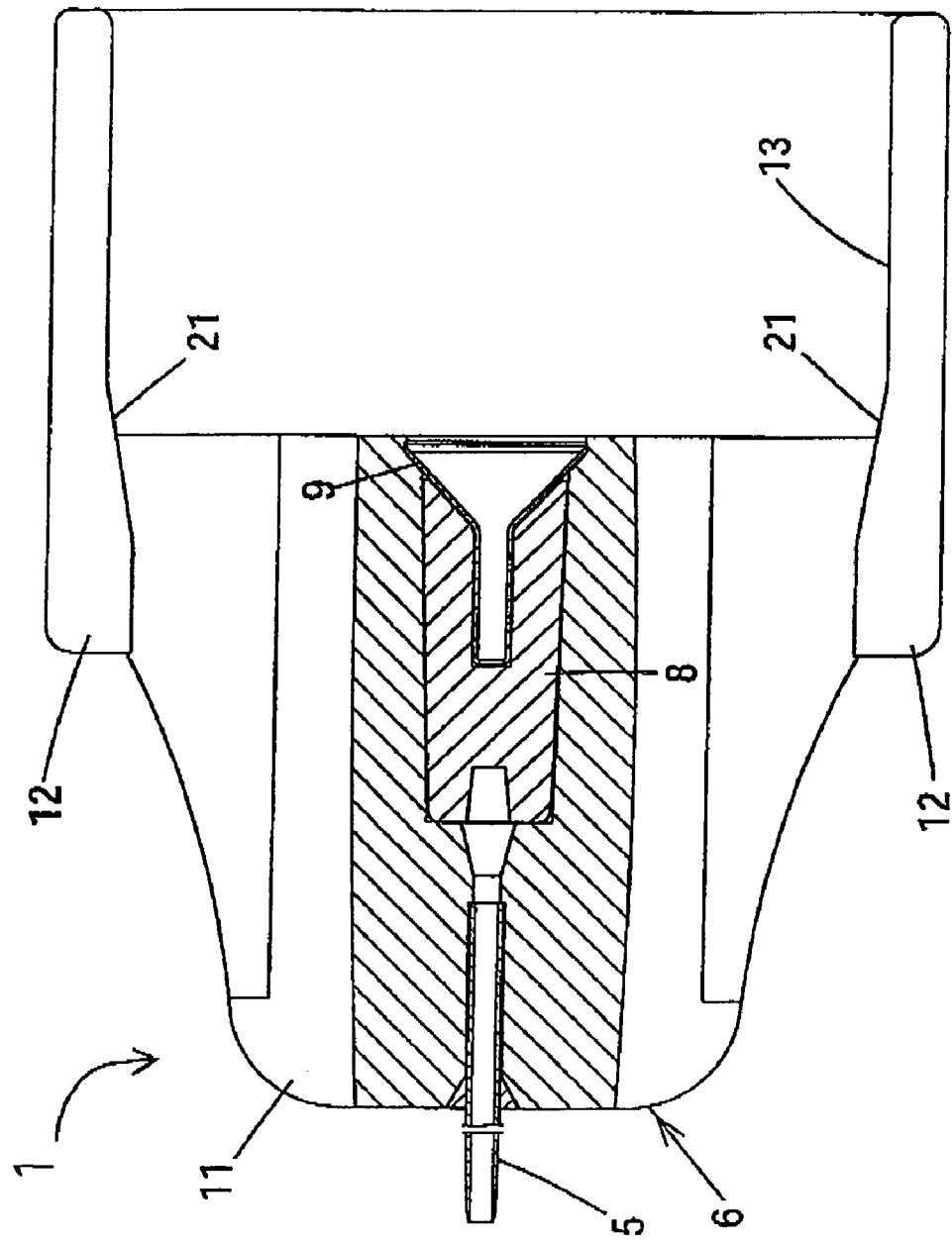
Figure 6:
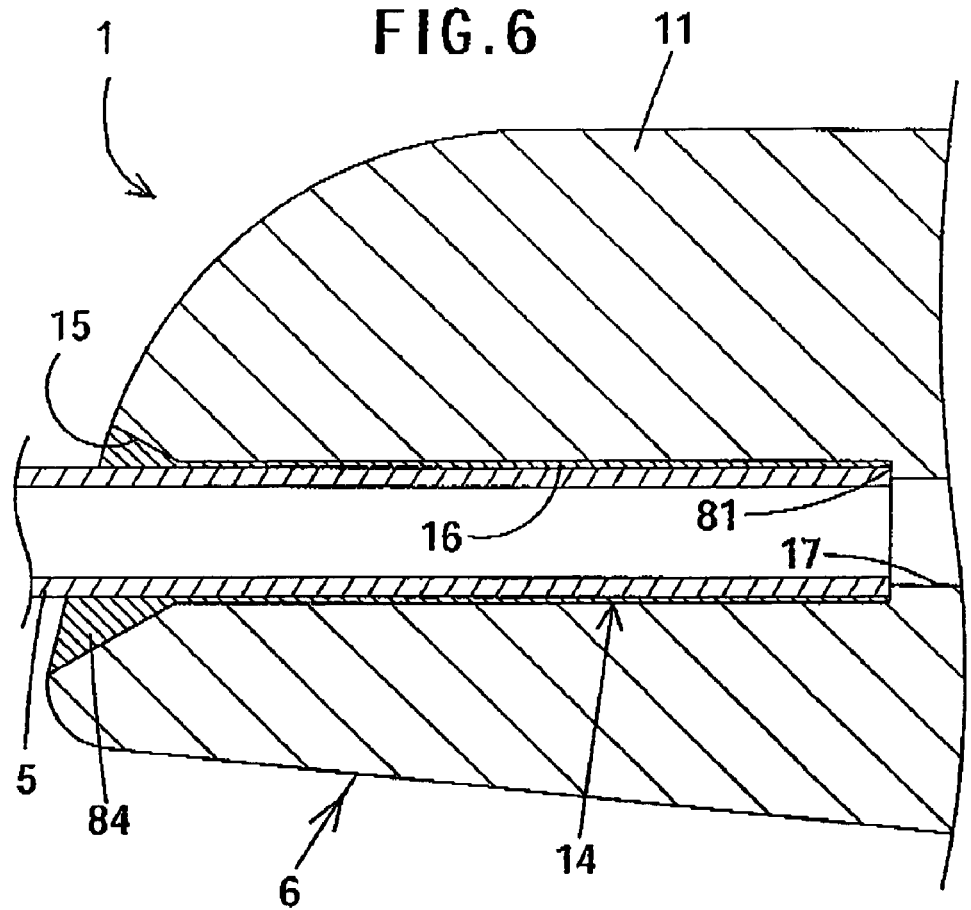
Figure 7:
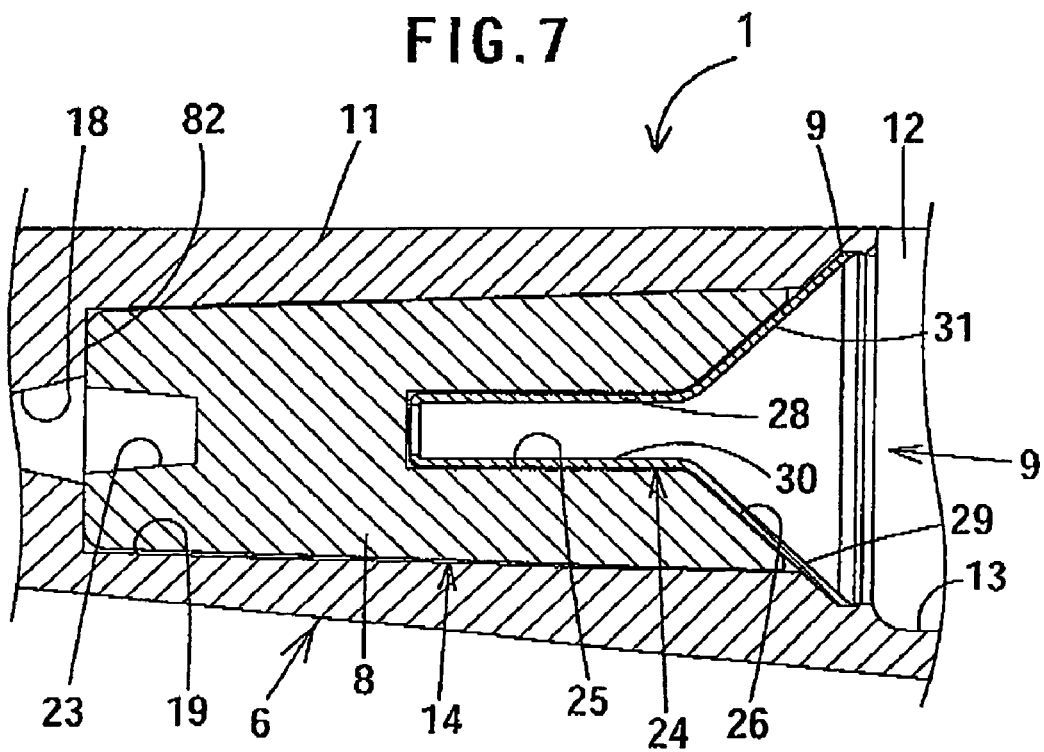

As shown also in FIG. 5 to FIG. 7, the cannula housing 1 includes a catheter (also referred to herein as soft cannula, outer needle, shielding needle, or catheter tube) 5, catheter hub (also referred to herein as indwelling needle base, outer needle base, or shielding needle base) 6, a plug 8, and a guide (also referred to herein as a caulking pin for guiding) 9.

The catheter 5 is disposed (substantially) in the axial direction, and formed into an elongated transparent (translucent) hollow (tubular) body having openings at its distal and proximal ends. The catheter 5 has flexibility and is formed integrally of plastic material (resin material). The plastic material includes, for example, thermoplastic resin. The thermoplastic resin used here is, preferably, polytetrafluoroethylene (PTFE), ethylene-tetrafluoroethylene copolymer (ETFE), polyurethane (PU), tetrafluoroethylene-perfluoroalkyl-vinyl-ether copolymer (PFA), polypropylene (PP), polyethylene (PE), polyvinyl chloride (PVC), acrylonitrile-butadiene-styrene copolymer, polycarbonate, polyamide, polyoxymethylene, and more preferably, PTFE, ETFE, PP, and PU.

The catheter hub 6 includes an upwardly projecting central protrusion (projection) 11 at the lateral center of the distal portion, upwardly projecting side protrusions (projections) 12 on the left and the right sides of the proximal portion, and a depression 13 depressed downward at the remaining portion. At the lateral center of the central protrusion 11, a through bore (insertion bore) 14 is formed so as to penetrate (substantially) in the axial direction. The through bore 14 includes a proximally tapered distal tapered bore 15, a large diameter bore 16 having an inner diameter constant in the direction of the axial center, a small diameter bore 17 having an inner diameter smaller than the large diameter bore 16, a distally tapered proximal tapered bore 18 (see FIG. 7), and a connecting port 19 for feeding liquid being larger in inner diameter than that of the proximal end of the proximal tapered bore 18, all in communication with each other in the above described sequence toward the proximal end. The large diameter bore 16 and the small diameter bore 17 are in communication with each other in a shouldered shape, and a distal abutment surface 81 of a distally facing planar surface is formed at the boundary thereof. The proximal portion of a catheter 5 is inserted into the distal tapered bore 15 and the large diameter bore 16 from distal ends thereof, and the proximal end of the catheter 5 abuts against the distal abutment surface 81. By forming the distal tapered bore 15 in the through bore 14, the catheter 5 can easily be inserted into the through bore 14. The proximal tapered bore 18 and the connecting port 19 are in communication with each other in a shouldered shape, and a proximal abutment surface 82 of a proximally facing planar surface is formed at the boundary thereof. The connecting port 19 may have a constant inner diameter in the direction of the axial center, or tapered toward the distal end at a small taper ratio depending on the cases. The inward side surfaces of the side protrusions 12 serve as guiding surfaces 20, and the axially central portions of the guiding surfaces 20 are beveled surfaces 21 extending inwardly as it proceeds to the distal end. The catheter hub 6 is integrally formed of plastic material (resin material), and the plastic material is preferably the same as those of the catheter 5, polyethersulfone (PES), or ABS resin, and more preferably, PP, PE, PES, PVC, and ABS resin.

The catheter 5 is fixed to a catheter hub 6 by any one of the following means. The first means is shown in FIG. 6, and configured as follows. By recent development of technologies, materials (substances) that can hardly be adhered, such as fluorinated tube, can be adhered to other materials (substances) by modifying the property of (processing) the surface, for example, by roughening. Therefore, the catheter 5 is formed of fluorine containing material, such as PTFE, ETFE, PFA. Then, surface processing such as corona discharge or plasma discharge is applied on the outer surface (the surface) of the catheter 5 to provide roughness on the above-described outer surface for obtaining a good adhesive property with respect to the catheter hub 6. Subsequently, the catheter 5 is adhered to the inner surfaces of the distal tapered bore 15 and the large diameter bore 16 of the catheter hub 6 with an acrylic adhesive agent 84.

The second means is as follows. At present, the catheter 5 is formed of materials such as ETFE or PU for reducing the possibility of giving damages to the patient after insertion. In particular, PU is low in softening temperature, and hence it is liable to be softened at the body temperature when the catheter 5 is indwelled under the skin of the patient, which advantageously reduces uncomfortable feeling when the catheter 5 is indwelled. In addition, PU is good in adhesive property in comparison with the fluorine containing materials. Therefore, the catheter 5 is formed of PU, and adhered on the inner surfaces of the distal tapered bore 15 and the large diameter bore 16 of the catheter hub 6 with the adhesive agent 84.

By fixing the catheter 5 to the catheter hub 6 with the adhesive agent 84 as described above, the process steps for fixing the catheter 5 can be reduced in comparison with the method of fixing the catheter 5 using a fixing pin as in the related art and, in addition, the fixing pin can also be eliminated, so that the manufacturing cost of a cannula housing 1, that is, the administration set can be reduced.

Since the fixing pin is not used for fixing the catheter 5 as in the related art, the risks of cracking of the catheter hub 6 or breakage of the catheter 5 by the tip of the fixing pin, or leakage of liquid due to variation of machining accuracy of the fixing pin can be avoided.

The plug 8 is formed into substantially a columnar shape, and fitted and fixed into the connecting port 19 of the catheter hub 6 for sealing the connecting port 19. As an example of the above-described "fitted", the present invention employs "press-fitting", and hence the plug 8 is press-fitted into the connecting port 19. The term "press-fitting" means a state of "inserted in a state of being compressed in the axial and radial directions", and the reason to press-fit is for desirably sealing the connecting port 19 by bringing the outer surface of the plug 8 into press-contact (close contact) with the inner surface of the connecting port 19. However, even when the plug 8 is not press-fitted into the connecting port 19, as will be described later, the connecting port 19 is satisfactorily sealed by press-contact (close contact) of the plug 8 with the inner surface of the connecting port 19 by fitting (press-fitting and fixing) the guide 9 into a proximal bore 24 of the plug 8 and the connecting port 19 of the catheter hub 6. A distal bore 23 of truncated conical shape is punctuated from the center of the distal end surface of the plug 8 toward the proximal end, and the proximal bore (engaging bore) 24 is punctuated (formed) from the center of the proximal surface of the plug 8 toward the distal end. The proximal bore 24 includes a straight bore 25 formed on the distal side having a constant inner diameter in the direction of the axial center, and a tapered bore 26 is formed on the proximal side so as to be tapered toward the distal end. The plug 8 is formed of a resilient material, for example, rubber material such as isoprene rubber, silicon rubber, butyl rubber, thermoplastic elastomer, silicon elastomer, or latex.

The guide 9 has both a function for retaining (fixing) the plug 8, and a function for guiding an insertion needle of an insertion hub 2 or an infusion needle of an infusion hub 3 described later, and is fitted (press-fitted and fixed) into the proximal bore 24 of the plug 8 and the connecting port 19 of the catheter hub 6. As shown also in FIG. 8, the guide 9 is formed into a hollow body having openings at its distal and proximal ends, and is integrally formed with a cylindrical portion 28 to be inserted (press-fitted) into the straight bore 25 of the proximal bore 24, the tapered bore 26 of the proximal bore 24, and a tapered portion 29 to be press-fitted into the proximal end of the connecting port 19. The guide 9 is fixed to the catheter hub 6 and hence the plug 8 is fixed to the catheter hub 6 by the proximal edge of the tapered portion 29 being press-fitted and fitted into the inner surface of the plug 8 while resiliently deforming the proximal end of the connecting port 19. Therefore, the plug 8 is prevented from falling off the connecting port 19. The interior of the cylindrical portion 28 is a straight bore 30 having a constant inner diameter in the direction of the axial center, and the interior of the tapered portion 29 is a distally tapered bore 31. The axial centers of the straight bore 30 and the tapered bore 31 (substantially) align with the axial center of the connecting port 19 of the cannula housing 1. The inner surface of the tapered bore 31 guides the insertion needle and the infusion needle to the (substantially) axial center of the plug 8 when they are inserted into the plug 8, which will be described below. The inner diameter of the distal end of the tapered bore 31, that is, the smallest inner diameter, and the inner diameter of the straight bore 30 are slightly larger than, but close to, the outer diameters of the insertion needle and the infusion needle as described later. The guide 9 is integrally formed of stainless steel (SUS 304 is preferable), nickel-titan alloy and so on.

Figure 9:
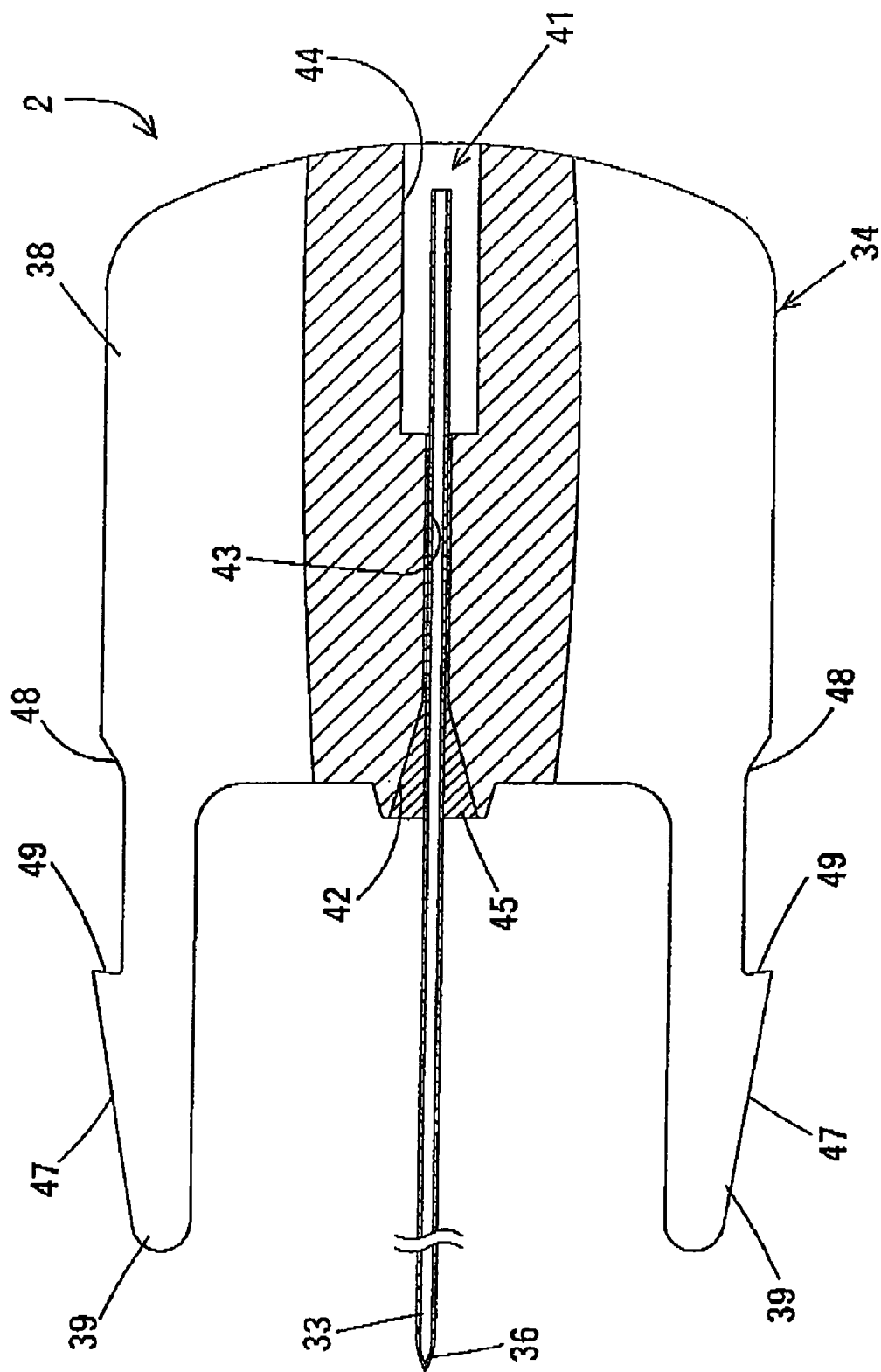

The insertion hub 2 is to be detachably connected to the cannula housing 1 from its proximal end and, as shown in FIG. 9, includes an insertion needle (also referred to herein as inner needle, or hard cannula) 33, and an insertion needle hub (also referred to herein as inner needle base) 34.

The insertion needle 33 is detachably inserted into a guide 9, a plug 8, and the catheter 5 of the cannula housing 1 and projects distally from the catheter 5. The insertion needle 33 is disposed substantially in the axial direction, and formed into a flexible elongated hollow body (tubular body) having openings at its axial ends. The distal end of the insertion needle 33 is cut obliquely with respect to the axial center thereof (bevel cut) and hence a distal opening edge 36 is beveled to provide a sharp cutting edge. The distal opening of the insertion needle 33 faces upward. The insertion needle 33 is integrally formed, for example, of stainless steel (SUS 304 is preferable), or nickel-titan alloy.

The insertion needle hub 34 is provided at the proximal portion of the insertion needle 33, and is to be detachably connected to the catheter hub 6 of the cannula housing 1 from its proximal end, and includes integrally formed a main body 38 and a pair of left and right engaging claws 39. The insertion needle hub 34 is formed of the same material as the catheter hub 6.

An insertion bore 41 for the insertion needle is formed at the lateral center of the main body 38 so as to penetrate (substantially) in the axial direction. The insertion bore 41 includes a proximally tapered bore 42, a straight bore 43 having a constant inner diameter in the direction of axial center, a depressed portion 44 having an inner diameter constant in the direction of the axial center and larger than the outer diameter of the straight bore 43, all communicated with each other arranged in above-described sequence toward the distal end. The insertion needle 33 is inserted into the insertion bore 41 from its distal end, and fixed to the inner surface of the tapered bore 42 and the straight bore 43 with an adhesive agent 45, so as to project distally from the insertion needle hub 34 to a large extent. By forming the tapered bore 42 in the insertion bore 41, the insertion needle 33 can be inserted easily into the insertion bore 41. There is a case that the insertion needle 33 is welded to the insertion needle hub 34. When connecting the insertion hub 2 to the cannula housing 1, the main body 38 is inserted from the proximal end of the depression 13 of the catheter hub 6, that is, behind the central protrusion 11 and between the side protrusions 12, so that the distal surface abuts against the proximal surface of the central protrusion 11.

The engaging claws 39 each constitute a locking mechanism for the insertion hub 2 in cooperation with the side protrusions 12 of the catheter hub 6, and project distally from the left and the right sides of the distal portion of the main body 38 so as to be capable of swinging in the lateral direction by resilient deformation of their own. The outward side surfaces of the distal portions of the engaging claws 39 are beveled surfaces 47 inclining inwardly as they proceed toward the distal end, and the proximal sides of the beveled surfaces 47 on the above-described outward side surfaces are formed with depressions 48 which are depressed inwardly, and the distal inner surfaces of the depressions 48 serve as engaging portions 49 having proximally facing planar surfaces, respectively. When connecting the insertion hub 2 into the cannula housing 1, the engaging claws 39, being guided by the guiding surface 20 of the catheter hub 6 and resiliently deformed inwardly, are inserted between the central protrusion 11 and the side protrusions 12 of the catheter hub 6. When the bevel surfaces 47 are moved distally of the side protrusions 12 of the catheter hub 6, they swing outwardly by their resilient recovery force, and the engaging portions 49 move distally of the side protrusions 12, so that an accidental disconnection of the insertion hub 2 from the cannula housing 1 is prevented. Disconnection of the insertion hub 2 from the cannula housing 1 can easily be done by holding both engaging claws 39 and swinging inwardly, moving the engaging portions 49 inwardly of the side protrusions 12 and moving the insertion hub 2 proximally of the cannula housing 1.

Figure 12:
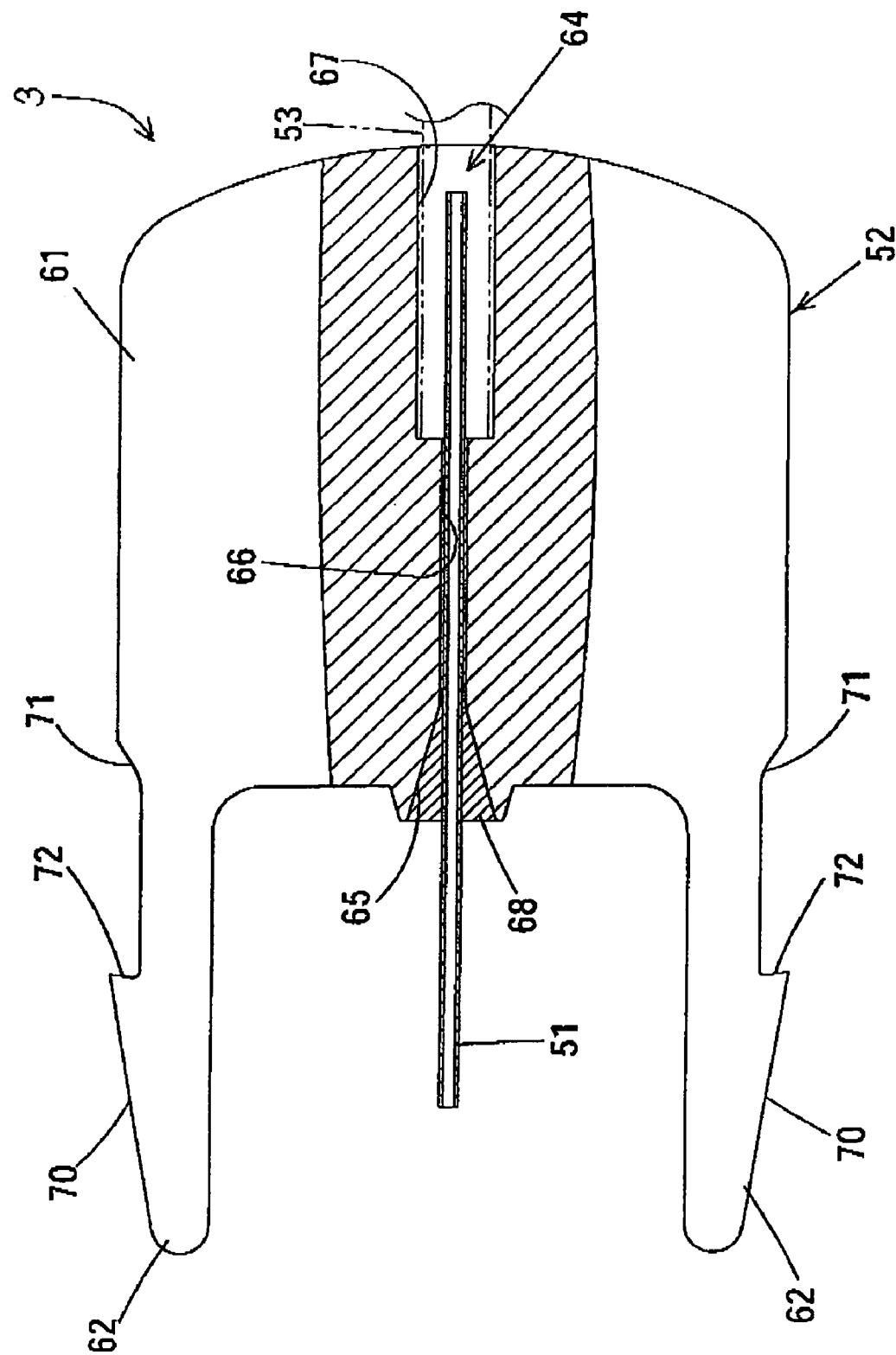
Figure 13:
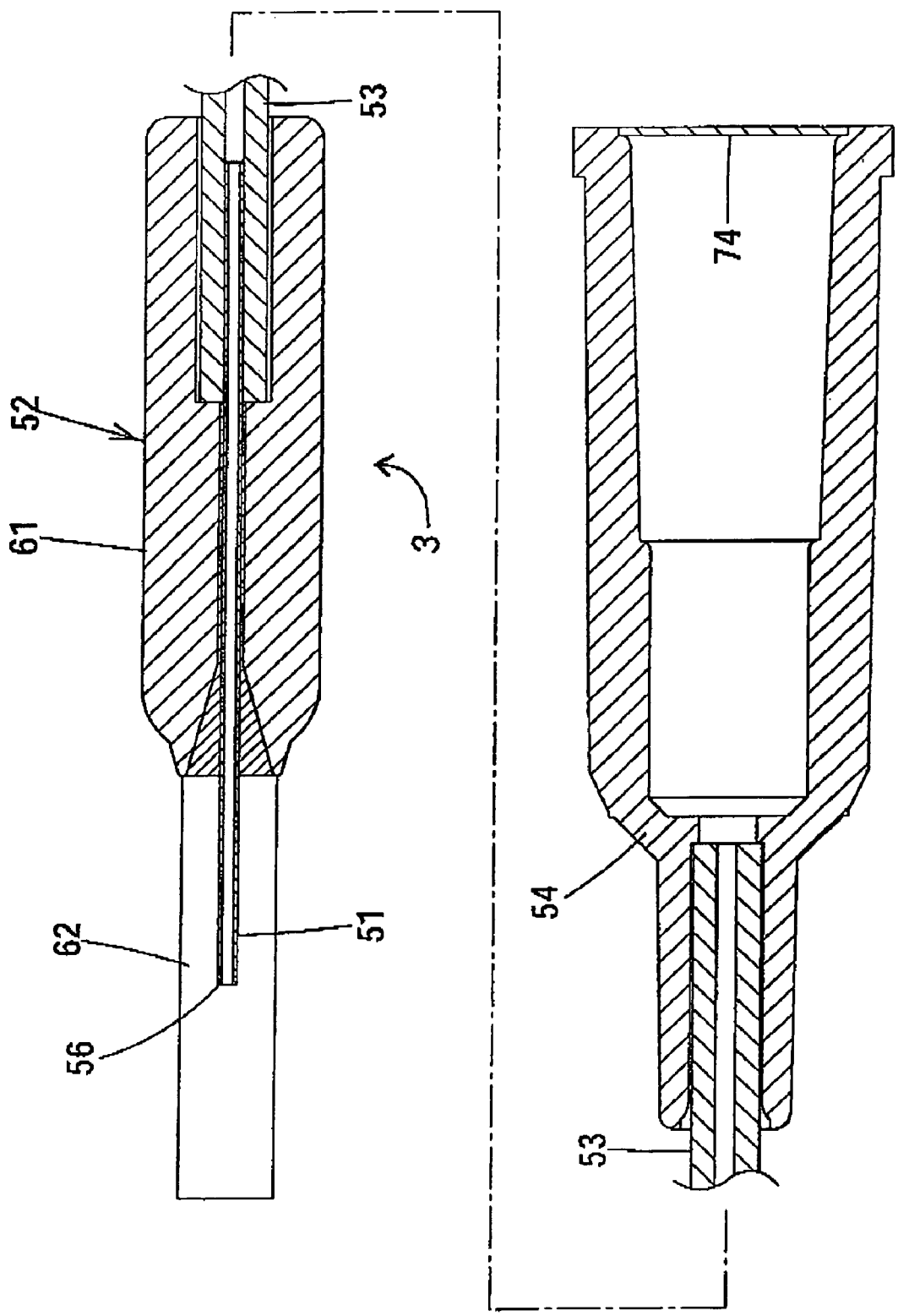

The infusion hub 3, which is to be detachably connected to the cannula housing 1 from its proximal end and, as shown in FIG. 12 and FIG. 13 as well, includes an infusion needle (also referred to herein as solution infusion needle) 51 for feeding liquid, an infusion tubing hub (also referred to herein as infusion needle base, or solution infusion needle base) 52, a tube (also referred to herein as liquid feeding line) 53, and a connector 54.

The infusion needle 51 is to be connected to the liquid feeding line, and detachably inserted into the guide 9 and the plug 8 of the cannula housing 1 from its proximal end, is disposed (substantially) in the axial direction, and is formed into an elongated hollow body (tubular body) having openings at its distal and proximal ends. The infusion needle 51 is integrally formed, for example, of stainless steel (SUS 304 is preferable) The infusion needle 51 is coated with lubricant such as silicone oil or the like applied thereon.

The infusion tubing hub 52, being provided at the proximal portion of the infusion needle 51, is to be detachably connected to the catheter hub 6 of the cannula housing 1 from its proximal end, and includes a main body 61 and a pair of left and right engaging claws 62 integrally formed with each other, similar to the insertion needle hub 34. The infusion tubing hub 52 is formed of the same material as the catheter hub 6 or the insertion needle hub 34.

Figure 14:
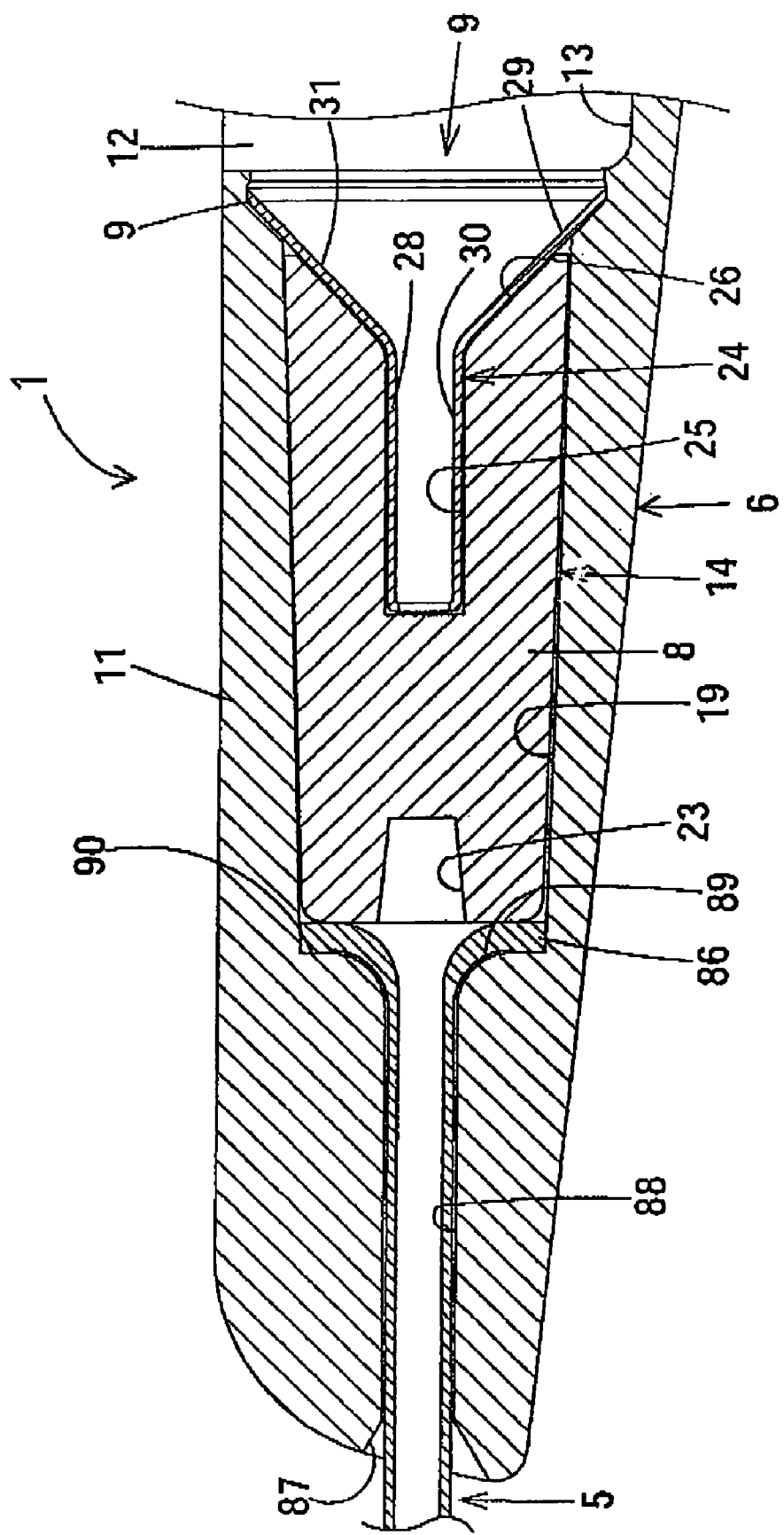
FIG. 14 and FIG. 15 show a second embodiment of the present invention.

An infusion needle insertion bore 64 is formed (substantially) in the axial direction so as to penetrate through the lateral center of the main body 61. As shown in FIG. 14, the insertion bore 64 includes a proximally tapered bore 65, a straight bore 66 having a constant inner diameter in the direction of the axial center, a tube fitting bore 67 having an inner diameter constant in the direction of the axial center and larger than that of the straight bore 66, all communicated with each other arranged in the above-described sequence toward the proximal end. The infusion needle 51 is inserted into the insertion bore 64 from its distal end, and fixed to the inner surfaces of the tapered bore 65 and the straight bore 66 with an adhesive agent 68 so as to project distally from the main body 61. By forming the tapered bore 65 in the insertion bore 64, the infusion needle 51 can easily be inserted into the insertion bore 64. There is also a case in which the infusion needle 51 is welded to the infusion tubing hub 52. When connecting the infusion hub 3 to the cannula housing 1, the main body 61 is inserted into the proximal portion of the depression 13 of the catheter hub 6, that is, behind the central protrusion 11 and between the side protrusions 12 from its proximal end, so that the distal surface abuts against the proximal surface of the central protrusion 11.

The engaging claws 62 each constitute a locking mechanism for the insertion hub 3 in cooperation with the side protrusions 12 of the catheter hub 6, and project distally from the left and the right sides of the distal portion of the main body 61 so as to be capable of swinging in the lateral direction by resilient deformation of their own. The outward side surfaces of the distal portions of the engaging claws 62 are beveled surfaces 70 inclining inwardly as they proceed toward the distal end, and the proximal sides of the beveled surfaces 70 on the above-described outward side surface are formed with depressions 71 which are depressed inwardly, and the distal inner surfaces of the depressions 71 serve as engaging portions 72 having proximally facing planar surfaces, respectively. When connecting the infusion hub 3 to the cannula housing 1, the engaging claws 62, being guided by the guiding surface 20 of the catheter hub 6 and resiliently deformed inwardly, are inserted between the central protrusion 11 and the side protrusions 12 of the catheter hub 6. When the beveled surfaces 70 are moved distally of the side protrusions 12 of the catheter hub 6, they swing outwardly by their resilient recovery force, and the engaging portions 72 move distally of the side protrusions 12, so that an accidental disconnection of the infusion hub 3 from the cannula housing 1 is prevented. Disconnection of the infusion hub 3 from the cannula housing 1 can easily be done by holding both engaging claws 62 and swinging inwardly, moving the engaging portions 72 inwardly of the side protrusions 12 and moving the infusion hub 3 proximally of the cannula housing 1.

The tube 53 is an example of the liquid feeding line, and is transparent (translucent). The distal end of the tube 53 is fitted on the proximal portion of the infusion needle 51, and is fixed to the inner surface of the tube fitting bore 67 of the insertion bore 64 of the infusion tubing hub 52, for example, with adhesion or welding. The length of the tube 53 may be freely determined as needed depending on the location of the insulin administration pump (not shown). The tube 53 is integrally formed of plastic material.

The connector 54 is a hollow body having openings at its distal and proximal ends, and fitted onto the proximal end of the tube 53 in communication with each other, and is to be connected to an insulin administration pump directly or indirectly via a connecting line (member) such as a tube. The opening of the proximal end of the connector 54 is sealed by a sealing member 74 such as a filter or a lid member before connecting the connecting line to the connector 54. The connector 54 is integrally formed of the same material as the catheter hub 6.

Figure 1:
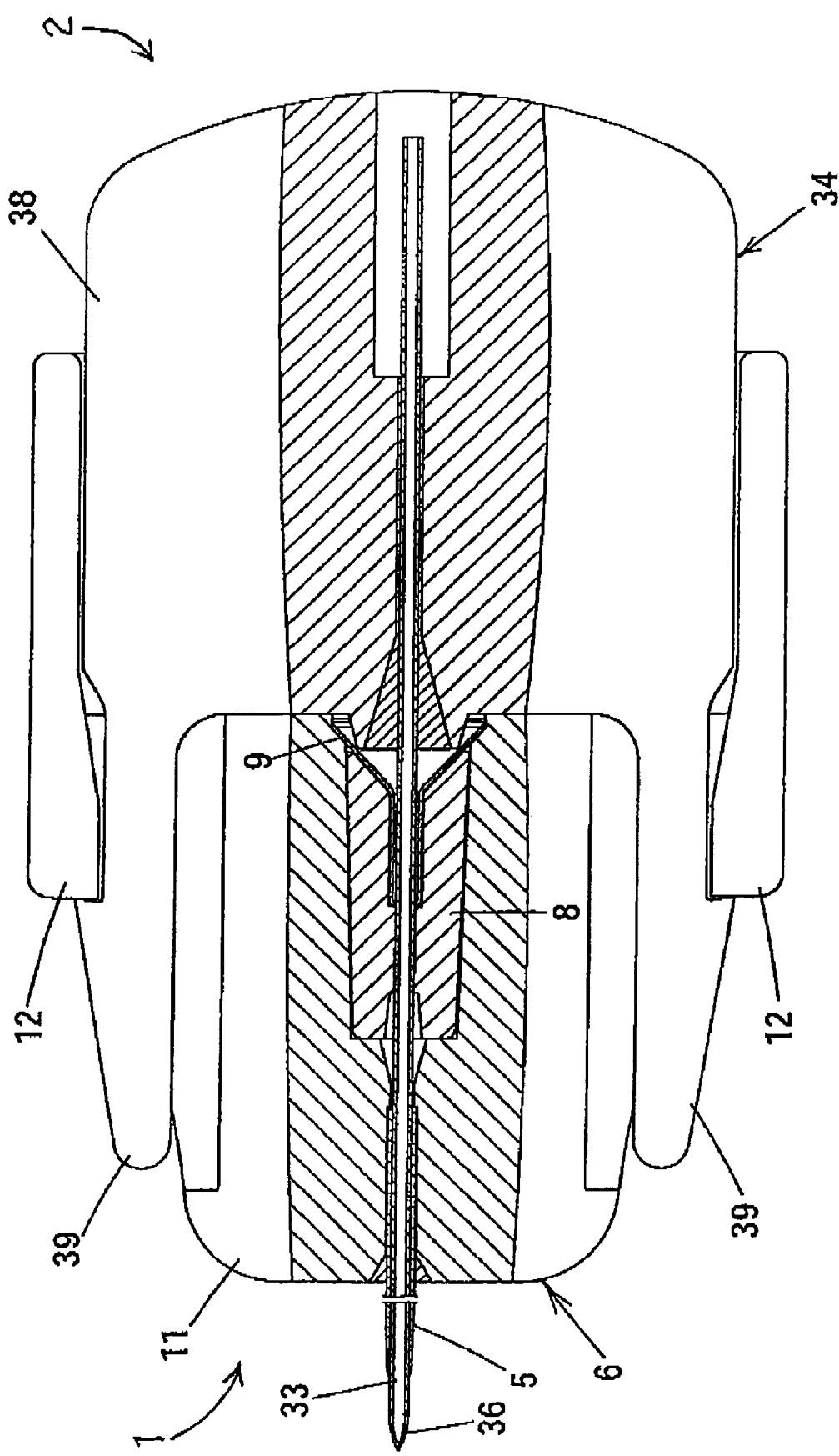
Figure 2:
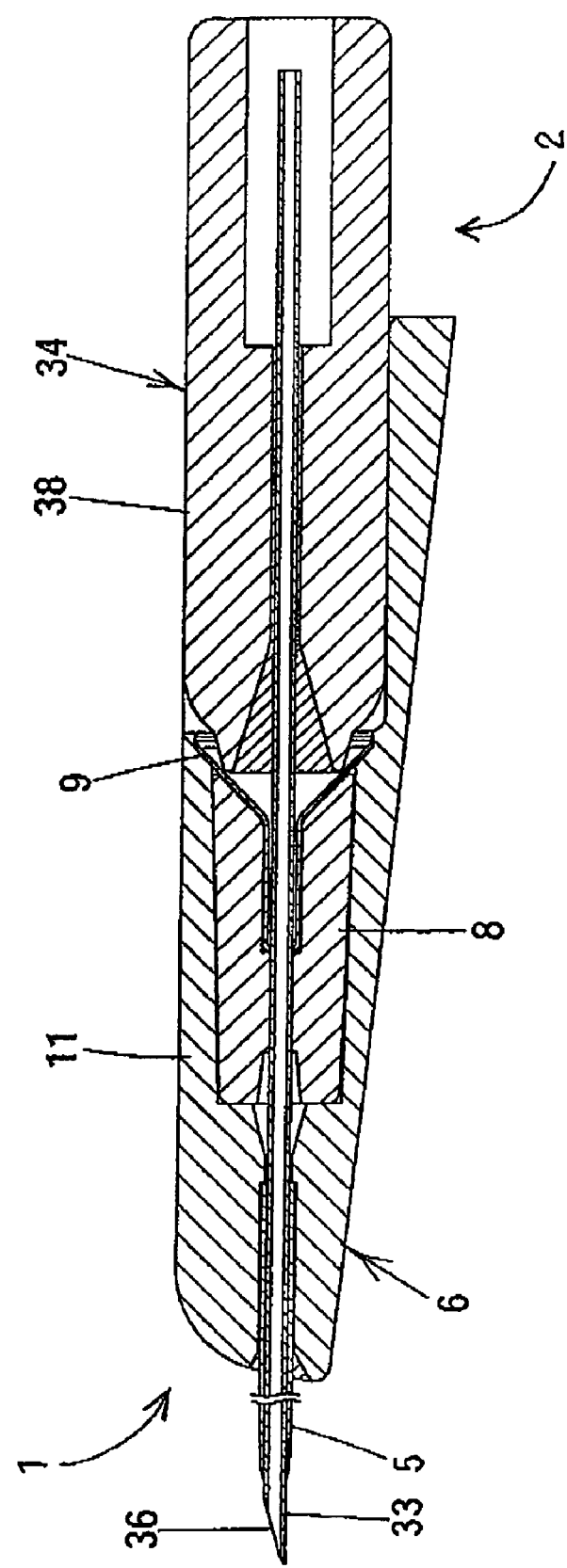
Figure 3:
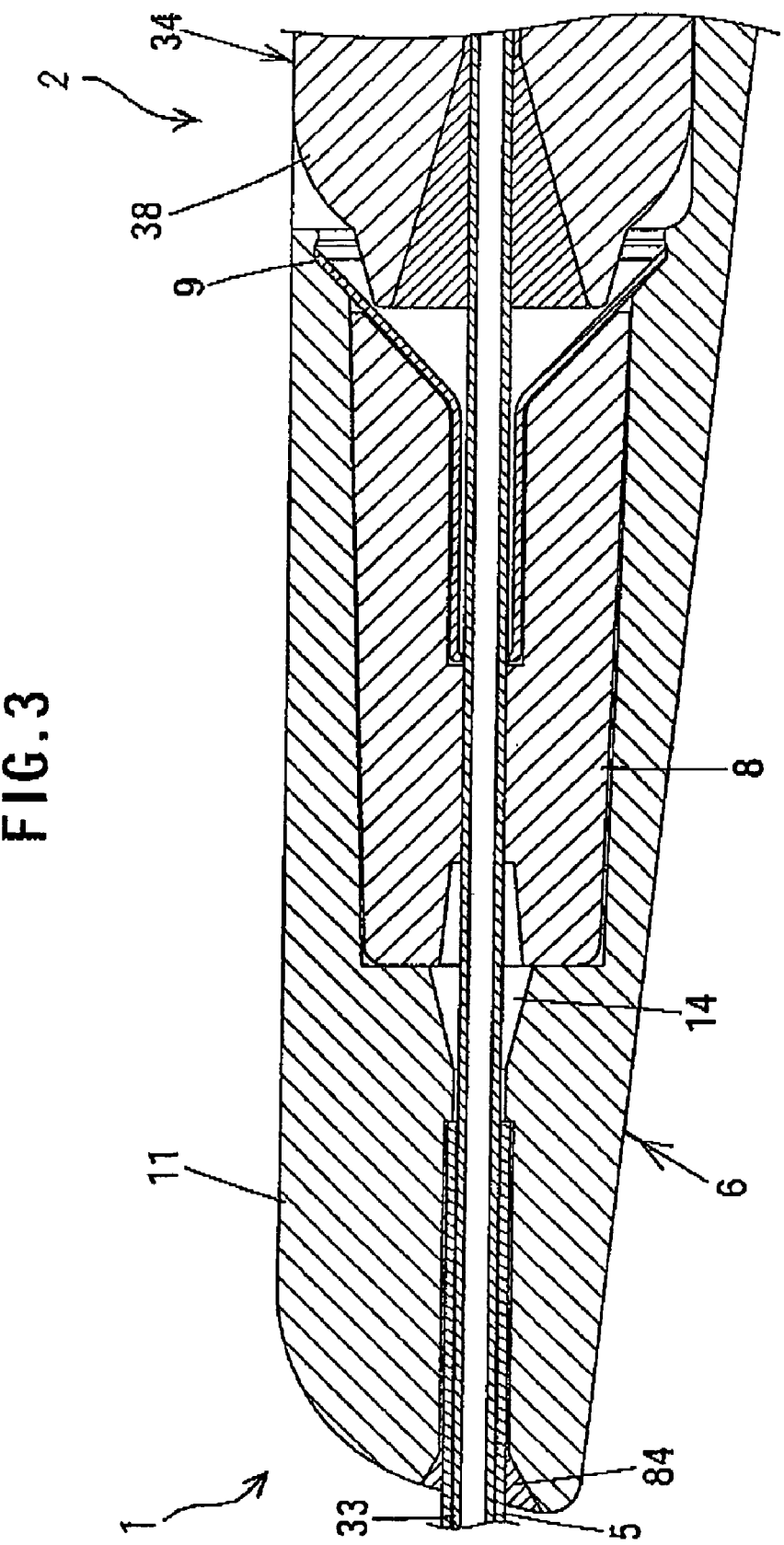
Figure 4:
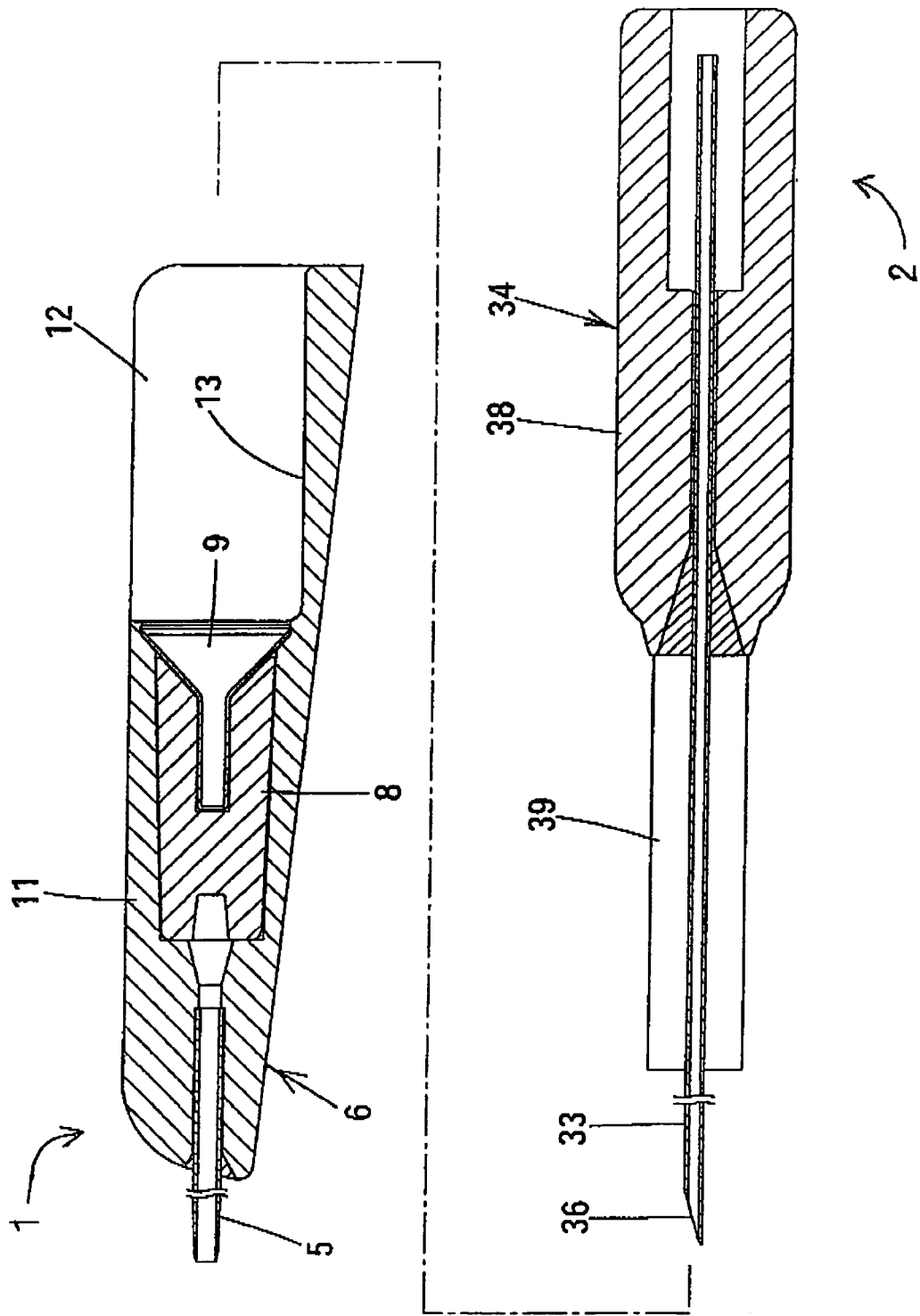

In the first embodiment described above, insertion of the catheter 5 under the skin of a patient is carried out by connecting the insertion hub 2 to the cannula housing 1, connecting the insertion needle hub 34 of the insertion hub 2 to the catheter hub 6 of the cannula housing 1 from its proximal end, and inserting the insertion needle 33 of the insertion hub 2 to the guide 9, the plug 8, and the catheter 5 of the cannula housing 1 from its proximal end as shown in FIG. 1 to FIG. 3, and when inserting the insertion needle 33 into the plug 8, the plug 8 is resiliently deformed.

In the related art, when inserting the insertion needle 33 into the catheter 5, since the fixing pin for fixing the catheter 5 to the catheter hub 6 and guiding the insertion needle 33 to the catheter 5 is provided at the proximal side of the catheter 5, the insertion needle 33 can easily be inserted into the catheter 5. However, in the configuration of the present embodiment, the fixing pin as described above is not provided.

However, in the present embodiment, the guide 9 is provided on the cannula housing 1, and the axial centers of a straight bore 30 and a tapered bore 31 of the guide 9 are (substantially) aligned with the axial center of the connecting port 19 of the cannula housing 1, and the inner diameter of the distal end of the tapered bore 31, that is, the smallest inner diameter thereof, and the inner diameter of the straight bore 30 are slightly larger than the outer diameter of the insertion needle 33. Therefore, when inserting the insertion needle 33 as described above, the sharp edged distal end of the insertion needle 33 is guided by the inner surface of the tapered bore 31 of the guide 9 and hence is centered, and then is guided to the (substantially) axial center of the guide 9, that is, of the connecting port 19 so as to be easily inserted into the straight bore 30 of the guide 9. Accordingly, the insertion needle 33 can easily be inserted into (substantially) the axial center of the plug 8, and hence the insertion needle 33 projects distally from a distal depression 23 of the plug 8 and is easily inserted into the catheter 5.

In this manner, in a state in which the insertion hub 2 is connected to the cannula housing 1, the insertion needle 33 and the catheter 5 are inserted under the skin of the patient. Then, the insertion hub 2 is disconnected from the cannula housing 1 to pull out the insertion needle 33 from under the skin of the patient and from the cannula housing 1, and the catheter 5 is indwelled under the skin of the patient. In this case, the trace (puncture) formed by the insertion needle 33 on the plug 8 is sealed by the resilient recovering force of the plug 8. Therefore, the risk of leakage of blood from the connecting port 19 of the cannula housing 1 or entrance of outside air from the connecting port 19 into the through bore 14 may be eliminated.

Figure 10:
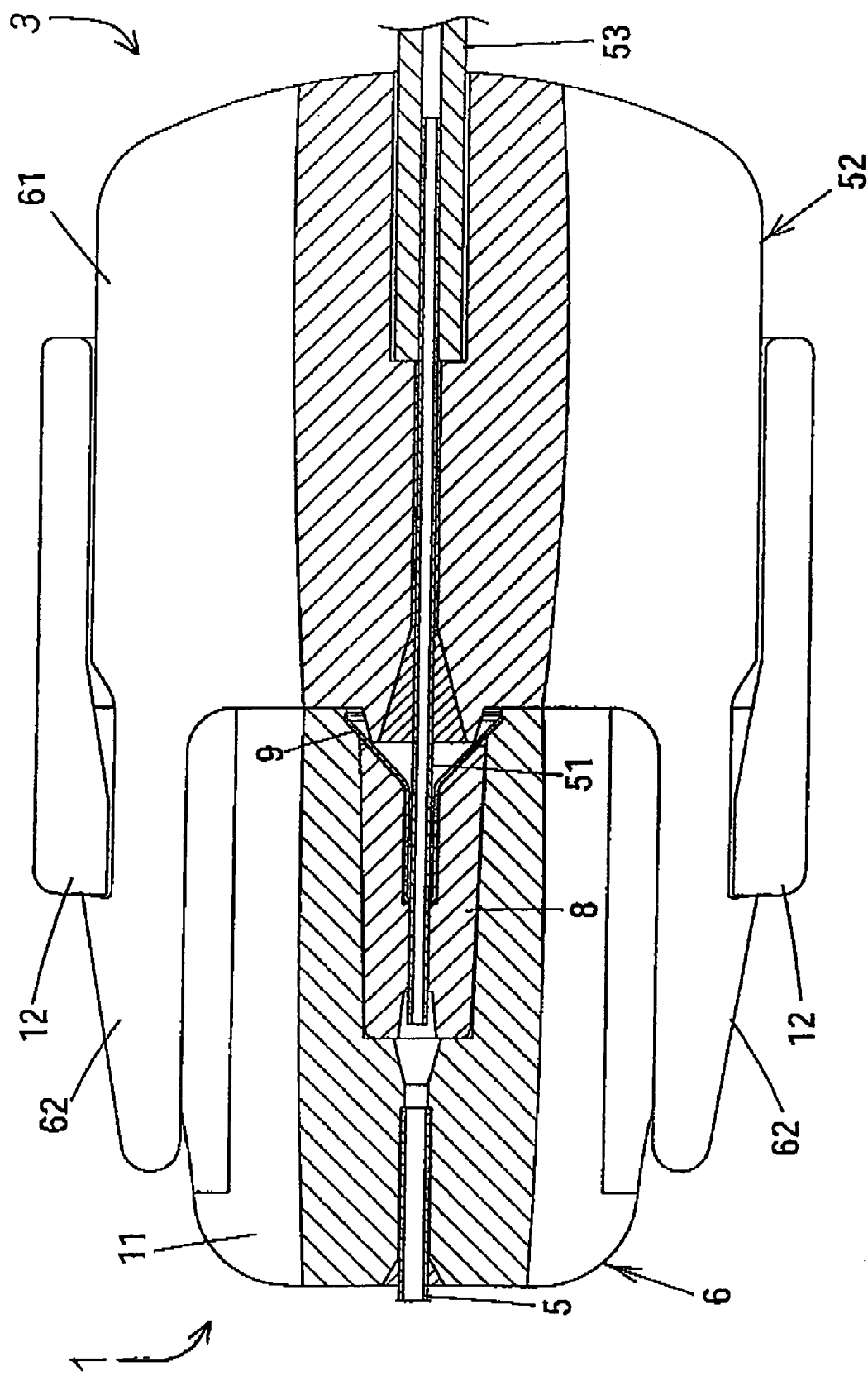
Figure 11:
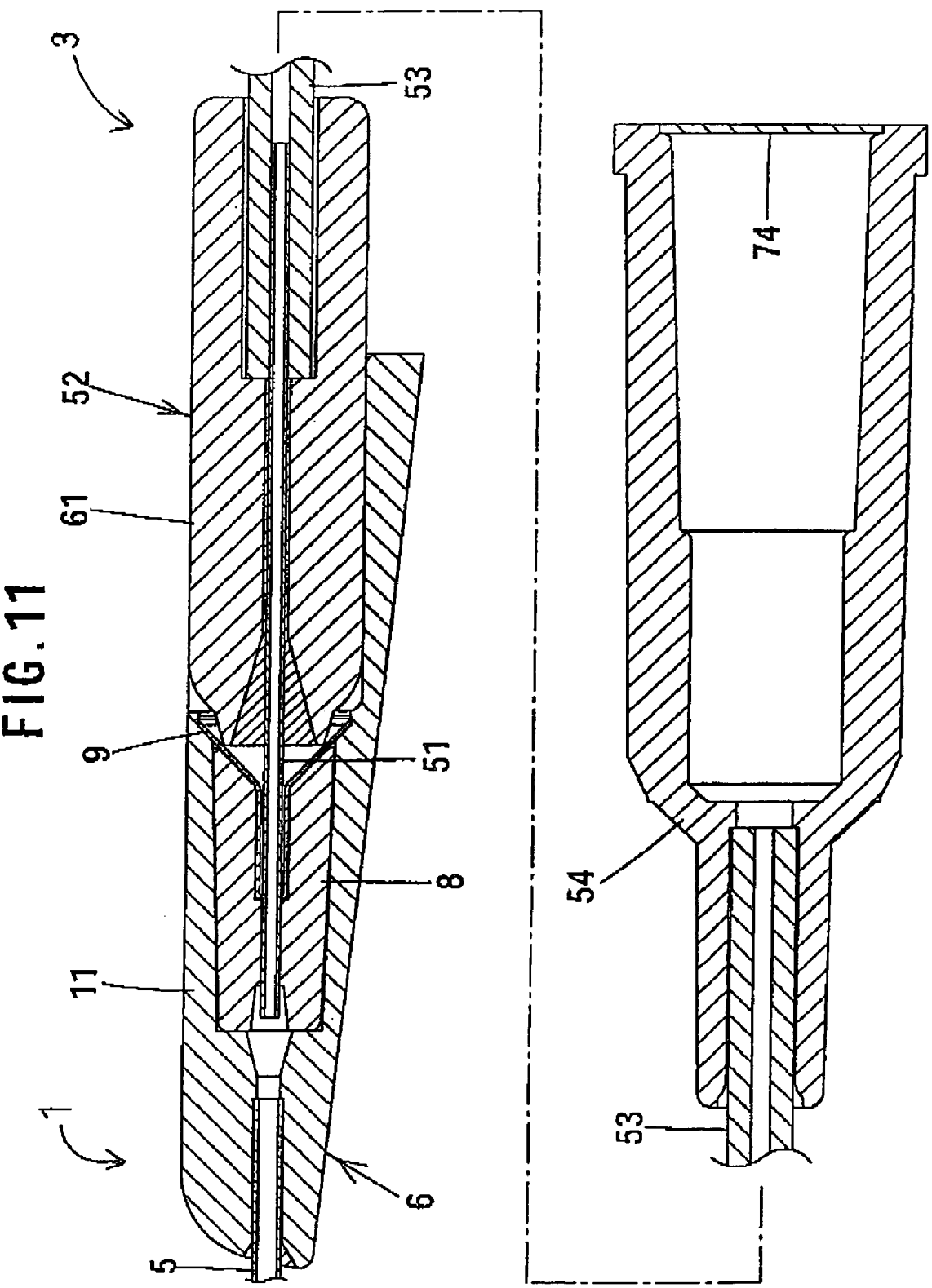

When insulin is administered discontinuously or continuously, as shown in FIG. 10 and FIG. 11, the infusion hub 3, to which the insulin administration pump is connected, is connected to the cannula housing 1, an infusion tubing hub 52 of the infusion hub 3 is connected to the catheter hub 6 of the cannula housing 1, and the infusion needle 51 of the infusion hub 3 is inserted into the guide 9 and the plug 8 of the cannula housing 1.

In this case, the guide 9 is provided on the cannula housing 1, the axial centers of the tapered bore 30 and the straight bore 31 of the guide 9 align (substantially) with the axial center of the connecting port 19 of the cannula housing 1, and the inner diameter of the distal end of the tapered bore 30, that is, the smallest inner diameter thereof, and the inner diameter of the straight bore 31 are slightly larger than the outer diameter of the infusion needle 51. Therefore, the infusion needle 51 is guided by the inner surface of the tapered bore 30 of the guide 9 and hence is centered, and then is guided to the (substantially) axial center of the guide 9, that is, of the connecting port 19 so as to be easily inserted into the (substantially) axial center of the plug 8.

In addition, the infusion needle 51 itself has little or no puncturing capability, and the risk that the user pricks his/her finger or hand is extremely low. Therefore, it is not necessary to provide a protective wall for surrounding the infusion needle 51 as shown in U.S. Pat. No. 6,056,718, and hence the infusion hub 3 can be downsized. In addition, since the infusion needle 51 is coated with lubricant applied thereon, the infusion needle 51 can be inserted into the trace in the plug 8 easily and smoothly.

By driving the insulin administration pump after the infusion needle 51 of the infusion hub 3 is inserted into the plug 8 of the cannula housing 1 as described above, the insulin can be administered into the patient's body discontinuously or continuously via the connector 54, the tube 53, the infusion needle 51, and the catheter 5 of the infusion hub 3 from the pump.

When the administration is completed, the infusion hub 3 is disconnected from the cannula housing 1 to disconnect the infusion tubing hub 52 of the infusion hub 3 from the catheter hub 6 of the cannula housing 1, and then the infusion needle 51 of the infusion hub 3 is pulled out from the plug 8 and the guide 9 of the cannula housing 1. In this case, the trace of the infusion needle 51 (that is, the trace of the insertion needle 33) of the plug 8 is closed by the resilient recovering force of the plug 8, and the risk of leakage of blood from the connecting port 19 of the cannula housing 1 or entrance of outside air from the connecting port 19 into the through bore 14 is eliminated.

Figure 15:
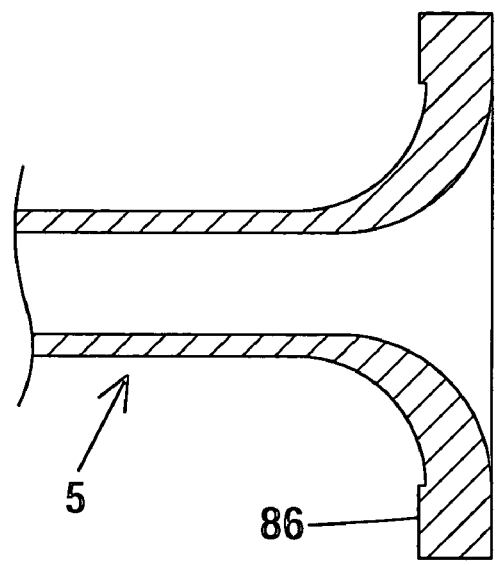

FIG. 14 and FIG. 15 show a second embodiment of the present invention. The proximal end of the catheter 5 is proximally flared so as to be enlarged toward the proximal end and the proximal end thereof is formed with a ring-shaped flange 86 so as to project radially outwardly. The through bore 14 of the catheter hub 6 includes a distally tapered bore 87, a straight bore 88 having an inner diameter constant in the direction of axial center, an enlarged bore 89 proximally enlarged in inner diameter corresponding to the shape of the proximal end portion of the catheter 5, and the connecting port 19, all in communication with each other arranged in the above-described sequence toward the proximal end. The enlarged bore 89 and the connecting port 19 are in communication with each other in a shouldered shape, and an abutment surface (welding surface) 90 of a distally facing planar surface is formed at the boundary thereof. The catheter 5 and the catheter hub 6 are formed of the same plastic material, for example, by injection molding. In this case, for example, the catheter 5 is formed of soft PP, and the catheter hub 6 is formed of hard PP. The flange 86 of the catheter 5 is welded, for example, by ultrasonic wave or the like, to the abutment surface 90 of the catheter hub 6 and the plug 8 abuts against the flange 86.

According to the present embodiment, an adhesive agent curing process required when an adhesive agent is employed (for example, heating, irradiation of ultraviolet (UV) light, leaving untouched for a long time in the room temperature, etc.) is not necessary and hence the number of process steps can be reduced, and the manufacturing cost for the cannula housing 1, that is, the administration set, can be reduced. In addition, by molding the catheter 5 and the catheter hub 6 with the same plastic material in the above-described molding step, the catheter 5 and the catheter hub 6 may have good mutual solubility and hence may easily be welded (by ultrasound waves). When high-priced fluorine containing materials as described above are used for the catheter 5 or the catheter hub 6, the manufacturing cost for the cannula housing 1 increases. However, by using low-priced PP as described above, the manufacturing cost for the cannula housing 1 can be reduced. A soft PP of a grade that can be used for various medical devices is already known.

Since the proximal end of the catheter 5 is flared so as to be enlarged toward the proximal end, when inserting the insertion needle 33 into the catheter 5, the insertion needle 33 can be guided on the inner surface of the proximal end portion of the catheter 5, and hence the insertion needle 33 can be inserted into the catheter 5 more easily.

Figure 16:
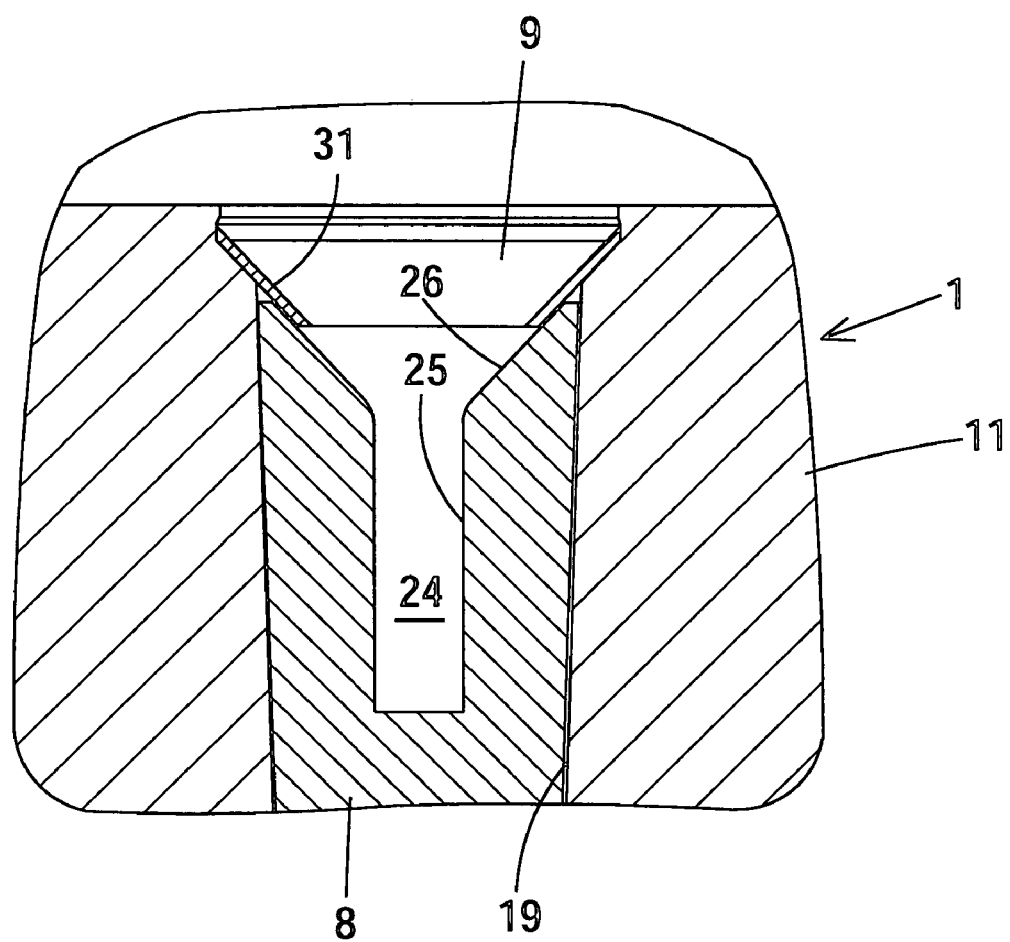
Figure 17A:
FIG. 17A is a side view of a guide in FIG. 16.
Figure 17B:
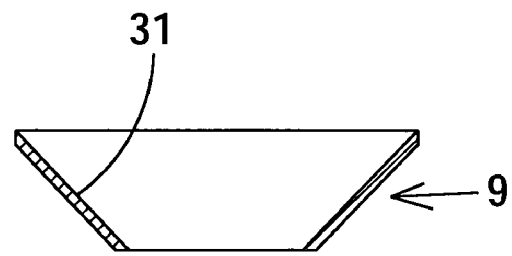
FIG. 17B is a vertical cross section of FIG. 17A.

FIG. 16 and FIG. 17 show a third embodiment of the present invention, in which the guide 9 has a configuration as in the first embodiment but having the cylindrical portion 28 removed from the guide 9 and being tapered toward the distal end.

In the above-described embodiments, the present invention is applied to an insulin administration set. However, the present invention can be applied also to (1) various indwelling catheter sets for solution infusion other than insulin, blood transfusion, blood collection, dialysis therapy, and so on.

What is claimed is:

1. An indwelling catheter set comprising:
    (a) a cannula housing; and
    (b) an insertion hub and an infusion hub to be detachably connected to the cannula housing,
    the cannula housing comprising:
    (a) a catheter disposed substantially in the axial direction and formed into a hollow body opened at its distal and proximal ends;
    (b) a catheter hub having a distal portion and a proximal portion and comprising a through bore extending substantially in the axial direction of the hub for inserting a proximal portion of the catheter therethrough, an upwardly projecting central protrusion at the lateral center of the distal portion, upwardly projecting side protrusions on the left and the right sides of the proximal portion, and a depression depressed downward at a remaining portion of the hub,
    wherein the catheter is adhered or welded to the catheter hub,
    and wherein a proximal portion of the through bore is formed as a connecting port for feeding liquid;
    (c) a plug formed of resilient material for sealing the connecting port and inserted into the connecting port from its proximal end; and
    (d) a guide inserted into a portion of the connecting port disposed proximally of the plug,
    wherein the guide is formed into a hollow body opened at its distal and proximal ends for preventing the plug from dropping off the connecting port,
    the guide allowing detachable insertion of an insertion needle of the insertion hub and an infusion needle of the infusion hub from proximal ends thereof,
    at least a proximal portion of the interior of the guide being formed into a tapered bore tapered toward the distal end of the guide, and
    at least the proximal portion of the interior of the guide having an inner surface for guiding the insertion needle and the infusion needle to a substantially axial center of the connecting port,
    the insertion hub comprising:
    (a) the insertion needle disposed substantially in the axial direction and formed into a hollow body opened at its distal and proximal ends, the insertion needle being detachably inserted into the plug and the catheter from proximal ends thereof when connecting the insertion hub to the cannula housing; and
    (b) an insertion needle hub provided at a proximal portion of the insertion needle, the insertion needle hub being detachably connected to the catheter hub from its proximal end when connecting the insertion hub to the cannula housing,
    the infusion hub comprising:
    (a) the infusion needle for feeding liquid disposed substantially in the axial direction and formed into a hollow body opened at its distal and proximal ends, the infusion needle being detachably inserted into the plug from its proximal end, when connecting the infusion hub to the cannula housing, so as to communicate with the catheter; and
    (b) an infusion tubing hub provided at a proximal portion of the infusion needle, the infusion tubing hub being detachably connected to the catheter hub from its proximal end when connecting the infusion hub to the cannula housing,
    wherein the insertion needle hub and the infusion tubing hub respectively comprise:
    (a) a main body to be detachably inserted between the side protrusions of the catheter hub when connecting the insertion hub or the infusion hub to the cannula housing; and
    (b) a pair of left and right engaging claws to be detachably inserted between the central protrusion and the side protrusions of the catheter hub and to be disposed distally of the side protrusions, when connecting the insertion hub or the infusion hub to the cannula housing, so as to be detachably engaged with the side protrusions.

2. An indwelling catheter set according to claim 1, wherein the catheter and the catheter hub are formed of the same plastic material by injection molding.

3. An indwelling catheter set according to claim 1, wherein the outer surface of the catheter is roughened by surface processing.

4. An indwelling catheter set according to claim 1, wherein a proximal end portion of the catheter is flared so as to be enlarged toward its proximal end.

5. An indwelling catheter set according to claim 1, wherein the guide comprises in the interior:
    (a) a straight bore forming a distal portion of the interior of the guide, the straight bore having an inner diameter substantially constant in the axial direction; and
    (b) the tapered bore forming the proximal portion of the interior of the guide.

* * * * *